United States Patent
Tseng

[11] Patent Number: 5,871,357
[45] Date of Patent: Feb. 16, 1999

[54] FIXING DEVICE FOR A REMOVABLE DENTURE

[76] Inventor: Hsien-Jung Tseng, 3F1. No. 142, Fraternity St., Hsin-Chu, Taiwan

[21] Appl. No.: 61,009

[22] Filed: Apr. 15, 1998

[51] Int. Cl.[6] .................................................. A61C 13/235
[52] U.S. Cl. ............................................. 433/189; 433/177
[58] Field of Search .................................... 433/177, 189, 433/172, 173

[56] References Cited

U.S. PATENT DOCUMENTS

| | | | |
|---|---|---|---|
| 4,204,321 | 5/1980 | Scott | 433/177 |
| 4,214,366 | 7/1980 | Laban | 433/189 |
| 4,290,755 | 9/1981 | Scott | 433/173 |
| 4,508,507 | 4/1985 | Jackson | 433/189 |
| 4,626,213 | 12/1986 | Shiner et al. | 433/189 |
| 4,787,851 | 11/1988 | Kusano et al. | 433/177 |
| 4,997,372 | 3/1991 | Shiner et al. | 433/189 |
| 5,049,072 | 9/1991 | Lueschen | 433/173 |
| 5,678,998 | 10/1997 | Honkura et al. | 433/189 |

FOREIGN PATENT DOCUMENTS

| | | | |
|---|---|---|---|
| 386047 | 3/1965 | Switzerland | 433/177 |
| 597843 | 4/1978 | Switzerland | 433/177 |
| 1665864 | 7/1991 | U.S.S.R. | 433/177 |

*Primary Examiner*—Ralph A. Lewis
*Attorney, Agent, or Firm*—Pro-Techtor International Services

[57] ABSTRACT

A fixing device for a removable denture mounted on the gingivals of an upper jaw or a lower jaw of a mouth. A stake is anchored in the base or root of the tooth, and a covering cup is mounted on the denture. An engaging member is placed in the cup chamber, the engaging member being a pair of magnetic members attracting each other because of their opposite magnetic polarities. The engaging member may also be a soft plastic annular member. When a ball head on the stake is engaged therein, the denture is fixed in place.

1 Claim, 7 Drawing Sheets

FIXING DEVICE FOR A REMOVABLE DENTURE

BACKGROUND OF THE INVENTION

1. Field of the Invention

The present invention is related to a fixing device for a removable denture, and especially for such a device which is usable for a whole denture set, a partial denture, or a single artificial tooth on the gingiva of an upper jaw or a lower jaw of a mouth. With the present invention, the firmness of engagement of the denture of a patient after it is mounted can be effectively increased. Convenience of mounting as well as for removal of the denture is also provided.

2. Description of the Prior Art

Clinical cases relative to teeth loosening and falling out by virtue of periodontosis or other factors occur in proportion to age. In other words, older people have higher rates of losing teeth than young people. However, there are also cases of losing teeth in accidents unrelated to age. In some cases, only one or two teeth are missing. In other cases, several or all of the teeth are missing. Dentists may deal with the patients' missing teeth with a partial denture. The dentists may make a set of dentures coincident with the curvature of the gingiva of the remaining teeth or on a jaw, so that the patients can properly chew food and have their appearance restored.

The currant art techniques of making dentures is to make a set of dentures (including the false teeth and the denture bases of the false teeth), and then adhere the upper and lower parts of the denture between the upper and lower jaws and the gingivas by adherence of saliva in a wearer's mouth and by a vacuum condition caused when the denture bases of the false teeth and the mucous membranes of the gingivas are engaged. However, the adherence of the saliva and the vacuum condition is generally not adequate, according to the experience of many users. The upper denture is subject to dropping when the wearer is biting food or opening his mouth wide. This mounting method is not applicable for those who only need mounting of a partial denture. Therefore, mounting of partial dentures or a single false tooth by the dentists is usually accomplished by a permanent installation, with the denture being permanently secured and mounted at the positions missing teeth. Permanent mounting of the dentures leads to difficulty in cleansing the dentures.

SUMMARY OF THE INVENTION

The primary object of the present invention is to provide a fixing device for a removable denture that can be used for mounting a whole set or a partial denture. The device is convenient for mounting as well as for removing and cleansing the dentures.

To achieve the above stated object, when the fixing device of the present invention is mounted for use, the areas missing teeth on the upper and lower jaws in the mouth of a patient must have sound bases of teeth provided for mounting; this is because the invention present anchors stakes in a root or base of a tooth to achieve the effect of convenience for mounting as well as removing a denture device. The device can be used to mount an entire set or a partial denture.

The present invention will be apparent in its practical structure and functions after reading the detailed description of the preferred embodiments thereof in reference to the accompanying drawings.

DETAILED DESCRIPTION OF THE PREFERRED EMBODIMENT

Figure 1:
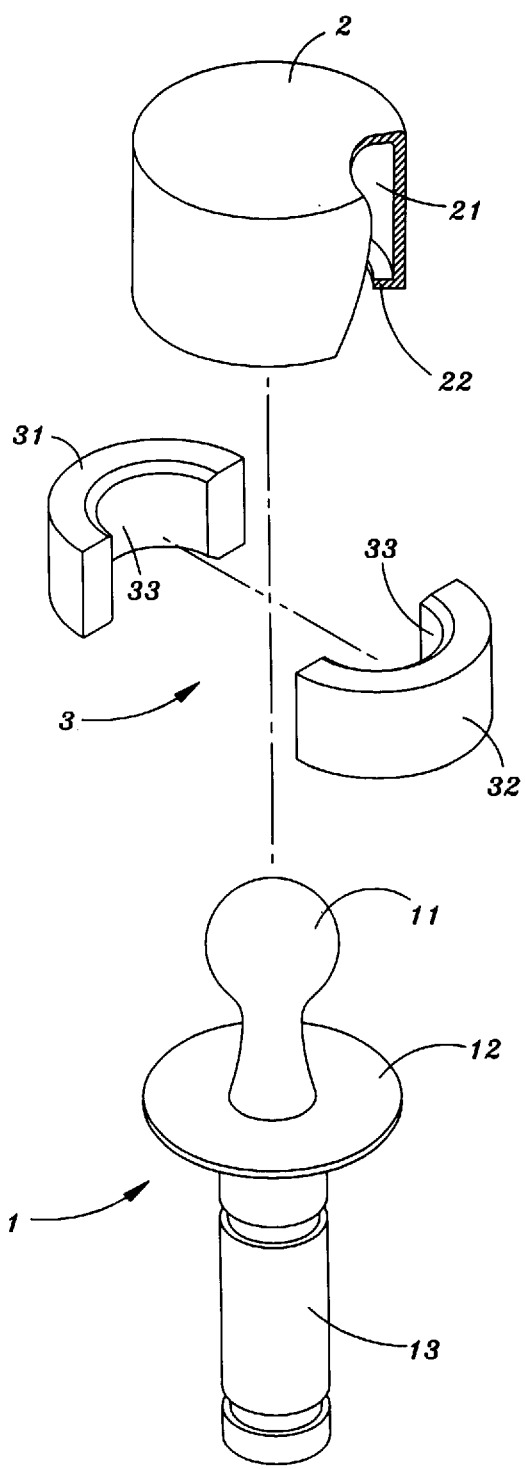
FIG. 1 is a perspective view of the fixing device for a removable denture of the present invention.

The fixing device for a removable denture provided in the present invention is made to have the shape as shown in FIG. 1, and is comprised of a stake 1, a covering cup 2 and an engaging member 3.

The stake 1 has a ball head 11, a disk-like shoulder 12 and a pin 13, all integrally formed.

The covering cup 2 has a cup chamber 21 and an inner annular rib 22 on the open end of the cup 2. The engaging member 3 is placed in the cup chamber 21.

The engaging member 3 is comprised of a pair of magnetic members 31, 32 which are separable (as shown in FIG. 1) and are each provided with a holding space 33. When the pair of magnetic members 31, 32 is placed in the cup chamber 21, the members 31, 32 attract each other because of their opposite magnetic polarities, and are connected (as shown in FIG. 3) so that the two holding spaces 33 are connected to form a round holding space.

Figure 2:
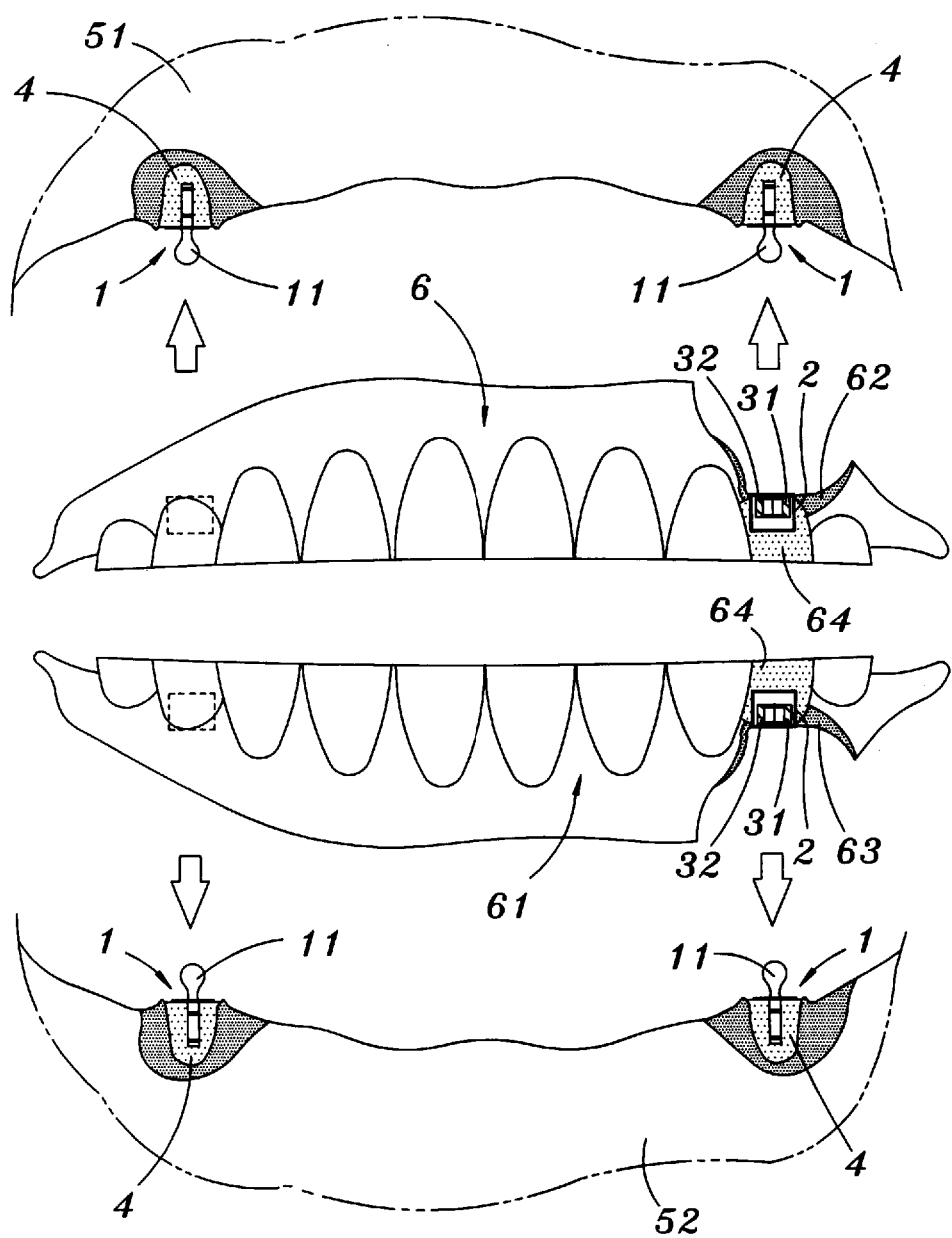
FIG. 2 is a schematic view of the present showing the fixing device used in mounting an upper and a lower denture.

When in use, a plurality of fixing devices of the present invention can be mounted on the dentures 6 and 61 for an upper jaw 51 and a lower jaw 52 (as shown in FIG. 2). The devices can also be used for partial false teeth (only two or three teeth or a partial denture) on the upper jaw 51 and the lower jaw 52. The pins 13 on the stakes 1 are positioned in the base of the tooth 4 so that the disk-like shoulders 12 are exactly at the level of the gum line, and so that the stakes 1 are firmly secured.

The ball heads 11 of the stakes 1 are exposed to the areas above the disk-like shoulders 12 for supporting and engaging the false teeth. The covering cups 2 provided therein with the engaging members 3 are embedded in the joints between the bases 62, 63 of the dentures 6 and 61 and the bodies of the false teeth 64. The openings of the covering cups 2 are exposed and perform the engaging function for mounting the ball heads 11 of the stakes 1.

Figure 3:
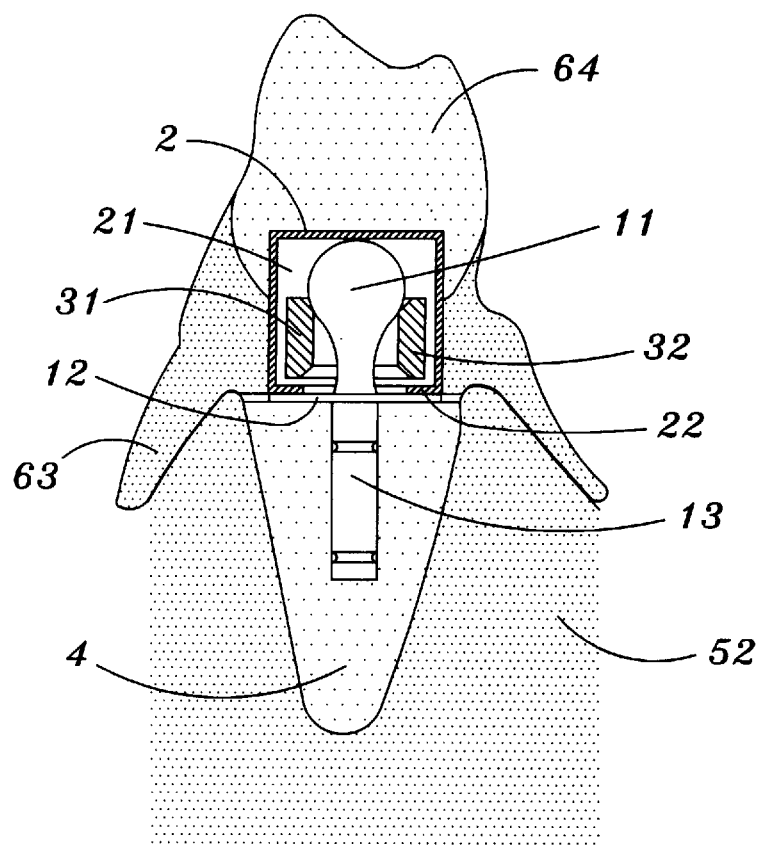
FIG. 3 is a schematic view showing assembly of the fixing device as depicted in FIG. 1.

As shown in FIG. 3, which discloses the first embodiment of the fixing device of the present invention, after a ball head 11 is inserted in the holding space 33 of the pair of half magnetic members 31, 32, the magnetic members 31, 32 attract each other by their opposite magnetic polarities. The ball head 11 is embedded in the holding space 33, and the inner annular rib 22 of the covering cup 2 prevents the magnetic members 31, 32 from dropping.

When the denture 61 is to be removed, the user needs only to pull on the denture 61 forcefully. This causes the ball head 11 to overcome the magnetic attraction between the magnetic members 31, 32, and the denture 61 can thus be removed. In this way, mounting and removal of the denture 61 is convenient.

Figure 4:
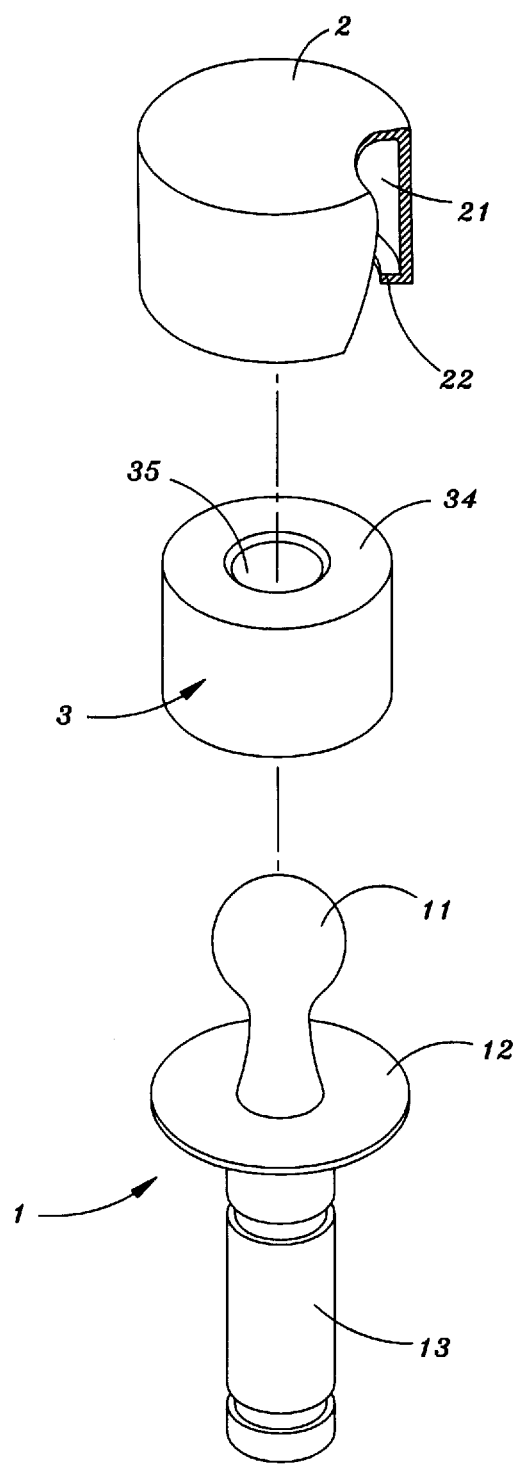
FIG. 4 is a perspective view of another embodiment of the fixing device for a removable denture of the present invention.
Figure 5:
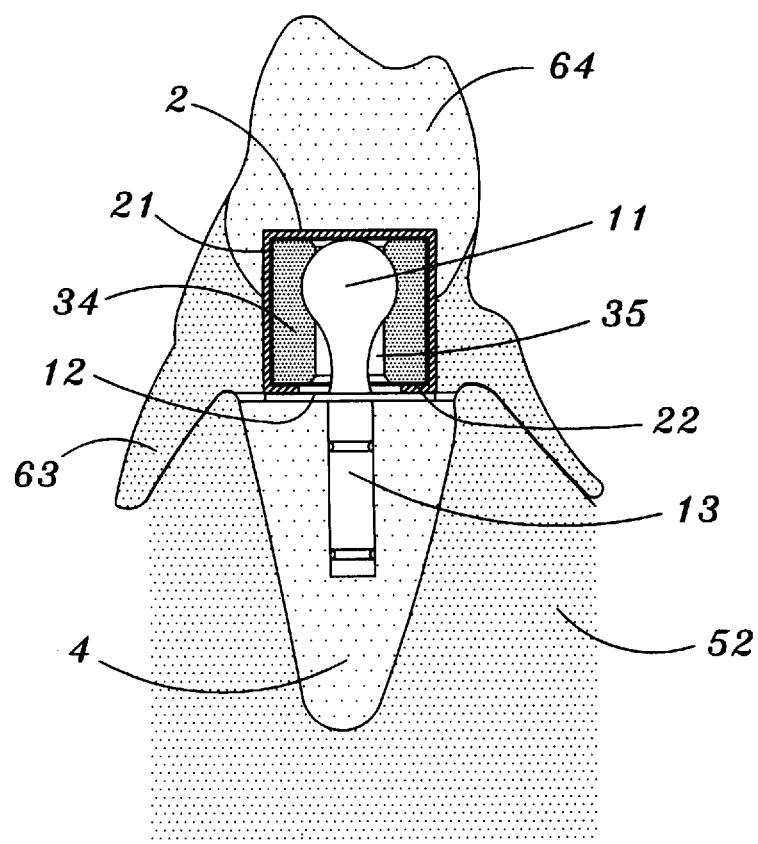
FIG. 5 is a schematic view showing assembly of the fixing device as depicted in FIG. 4.

In practicing the present invention, the engaging member 3 provided in the covering cup 2 is not limited to the mode of the magnetic attraction between the magnetic members 31, 32. In fact, the engaging member 3 can be a soft plastic annular member 34 (such as are shown in FIGS. 4 and 5). The annular member 34 is provided centrally with a shaped holding space 35 with a diameter slightly smaller than that of the ball head 11. The annular member 34 is also mounted in the cup chamber 21 of the covering cup 2, and is prevented by the inner annular rib 22 from dropping. When in use, the ball head 11 on the stake 1 in the holding space 35 is tightly clamped by the soft plastic annular member 34.

Figure 6:
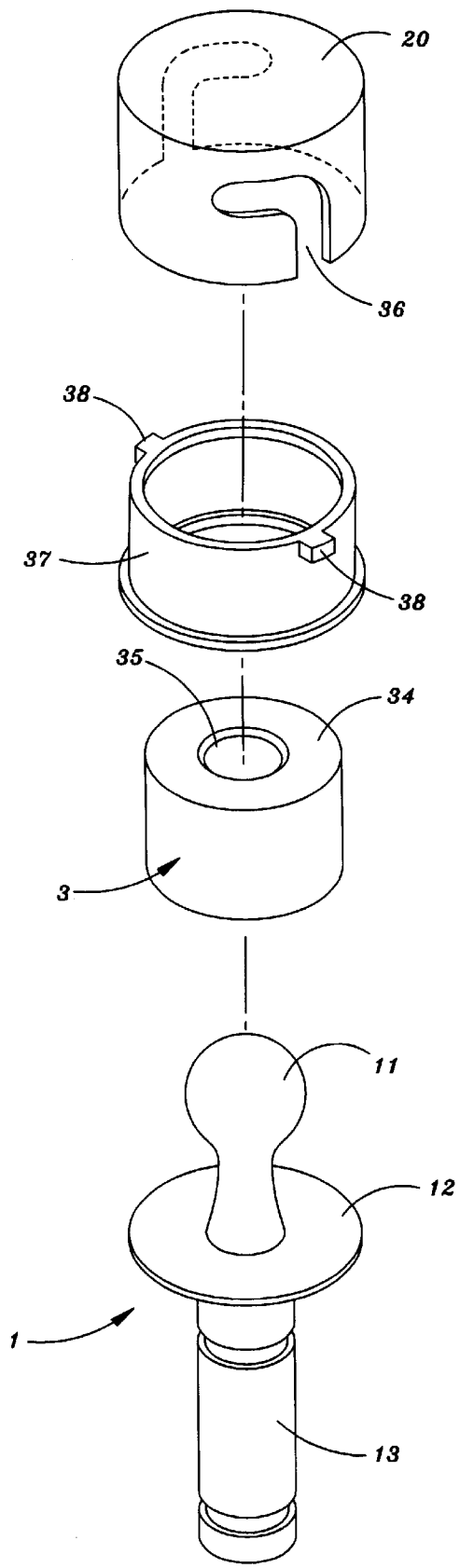
FIG. 6 is a perspective view of one more embodiment of the fixing device for a removable denture of the present invention.
Figure 7:
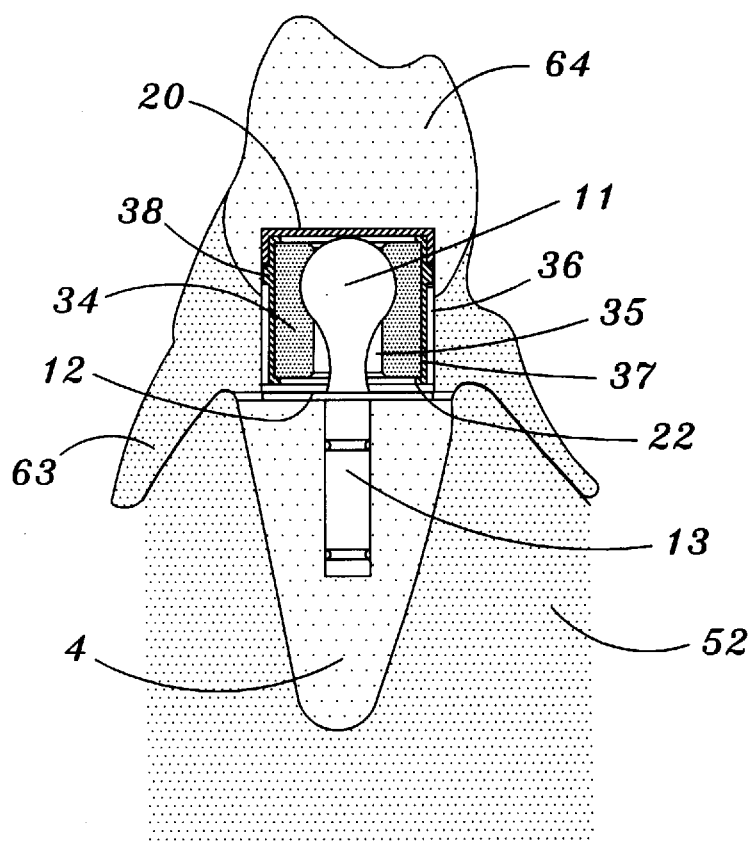
FIG. 7 is a schematic view showing assembly of the fixing device as depicted in FIG. 6.

When the annular member 34 is used in the engaging member 3, the wall of a covering cup 20 can be formed to have a pair of "L" shaped slots 36, as shown in FIGS. 6 and 7. The annular member 34 can be embedded in an annular collar 37 which is placed in the covering cup 20. The annular collar 37 is provided with a pair of lugs 38 which can be extended in the "L" shaped slots 36 so as to restrain the annular collar 37 with the annular member 34. This embodiment not only can effectively allow engagement and removal of the ball head 11 on the stake 1, but can also allow removal of the annular collar 37 from the covering cup 20 secured on the denture 61 to facilitate replacement of the annular member 34, which is subjected to wear in the annular collar 37.

Accordingly, the device of the present invention can be used to mount an entire set or partial denture on an upper jaw and a lower jaw of a mouth. The device provides effective as well as convenient mounting and removal of the denture. Convenience of removing for cleansing is also obtained.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A fixing device for a removable denture mounted on the gingivals of an upper jaw or a lower jaw of a mouth, said device is comprised of a stake, a covering cup and an engaging member, wherein:

said stake is adapted to be secured in the residual body of a tooth, a ball head of said stake is exposed to the area above the top of said residual body of said tooth, and wherein:

said covering cup is fixedly mounted on said denture, and has a cup chamber and an inner annular rib on the opening end thereof, said engaging member is placed in said cup chamber;

said engaging member comprises a pair of magnetic members which are separable and are each provided with a holding space, when said pair of magnetic members are placed in said cup chamber, they attract each other because of their opposite magnetic polarities, so that said denture having said covering cup and said pair of magnetic members can be engaged in said upper jaw or lower jaw, and said ball head of said stake is engaged in a holding space between said pair of magnetic members by magnetic attraction between said magnetic members, and said inner annular rib of said covering cup can prevent said magnetic members from dropping.

* * * * *